United States Patent [19]

Schmidt et al.

[11] 4,182,910

[45] Jan. 8, 1980

[54] METHOD OF PREPARING ORTHOACETIC ACID ALKYL ESTERS

[75] Inventors: Hans-Georg Schmidt, Niederkassel; Gerhard Daum; Wilhelm Vogt, both of Cologne, all of Fed. Rep. of Germany

[73] Assignee: Dynamit Nobel Aktiengesellschaft, Troisdorf, Fed. Rep. of Germany

[21] Appl. No.: 840,186

[22] Filed: Oct. 6, 1977

[30] Foreign Application Priority Data

Oct. 8, 1976 [DE] Fed. Rep. of Germany ....... 2645477

[51] Int. Cl.² ............................................. C07C 43/32
[52] U.S. Cl. .................................................. 568/595
[58] Field of Search .................................. 260/615 A

[56] References Cited

U.S. PATENT DOCUMENTS

| | | | |
|---|---|---|---|
| 2,527,494 | 10/1950 | Copenhaver | 260/615 A |
| 3,641,164 | 2/1972 | Sennewald et al. | 260/615 A |

FOREIGN PATENT DOCUMENTS 853405  11/1960  United Kingdom ................ 260/615 A

OTHER PUBLICATIONS

DeWolfe, Carboxylic Ortho Acid Derivatives, Academic Press, New York, 1970, pp. 2–11.

*Primary Examiner*—Howard T. Mars
*Attorney, Agent, or Firm*—Sprung, Felfe, Horn, Lynch & Kramer

[57] ABSTRACT

An improvement in the process for preparing an orthoacetic acid alkyl ester of the formula

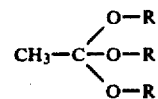

wherein R is a saturated, branched or un-branched, alkyl moiety of 1 to 8 carbon atoms by:

(a) contacting acetonitrile with an anhydrous alkanol having 1 to 8 carbon atoms and dry hydrogen chloride in the presence of an organic solvent to prepare the corresponding imidoester hydrochloride;

(b) thereafter contacting said imidoester hydrochloride in the acid-free state with an alkanol having 1 to 8 carbon atoms; and (c) removing by-product ammonium chloride from the resultant reaction mixture and distilling the reaction mixture to recover orthoacetic acid alkyl ester, the improvement residing in (d) employing as the organic solvent an inert solvent having a dielectric constant measured at 25° C. of 2.6 or less; and (e) contacting said imidoester hydrochloride in step (b) with an alkali metal or alkaline earth metal alcoholate before contacting the same with said alkanol.

Also disclosed is a process in which steps (a) and (b) are performed coterminously without isolation or recovery of the intermediate imidoester hydrochloride.

8 Claims, No Drawings

METHOD OF PREPARING ORTHOACETIC ACID ALKYL ESTERS

BACKGROUND OF THE INVENTION

1. Field of the Invention

This invention is directed to preparation of orthoacetic acid alkyl esters. More especially, this invention is directed to the preparation of such orthoacetic acid alkyl esters from acetonitrile, dry hydrogen chloride and an anhydrous alkanol followed by alcoholysis of the resultant intermediate imidoester hydrochloride. This invention is particularly concerned with the supression of secondary reactions which reduce the yields of the desired orthoacetic acid alkyl ester. This invention is therefore particularly concerned with the realization of sufficiently high yields or orthoacetic acid alkyl esters through such a route that the process can be economically performed on a commercial scale.

2. Discussion of the Prior Art

The preparation of orthoacetic acid alkyl esters of the formula $$CH_3-C\begin{matrix}O-R\\|\\-O-R\\|\\O-R\end{matrix}$$

in which R is a saturated, branched or unbranched, alkyl moiety of 1 to 8 carbon atoms is known. Furthermore, it is known to react acetonitrile with the corresponding anhydrous alcohol and dry hydrogen chloride in a two-step process in the presence of an organic solvent, the reaction to the corresponding imidoester hydrochloride taking place in the first step according to equation I below. In the second step the imidoester hydrochloride intermediate is subjected, while in the acid-free state, to an alcoholysis whereby the desired orthoacetic acid alkyl ester is formed in admixture with by-product ammonium chloride. The ammonium chloride is removed and following the ammonium chloride removal the reaction product is subjected to distillation in order to recover the desired orthoacetic acid alkyl ester. The equations for the process are as follows:

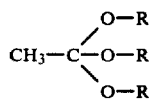

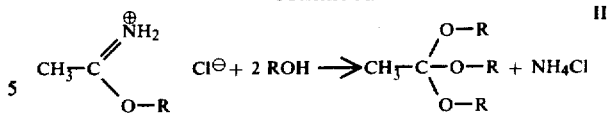

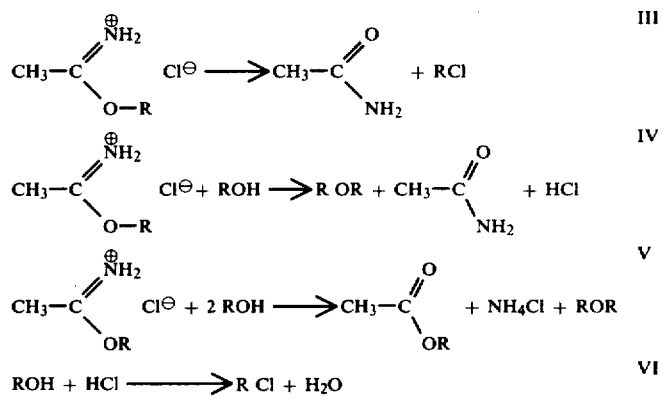

The preparation of orthocarboxylic acid esters by the reaction of carboxylic acid nitriles with alkanols and hydrogen chloride to form the corresponding imidoalkyl ester hydrochloride and the alcoholysis of the latter, is known (cf. H. Meerwein in Houben-Weyl, Vol. 6/3, pages 300–324, 1965). The yields in this very generally applicable method are impaired to one extent or another by a number of secondary reactions. The imidoalkyl ester hydrochloride is very sensitive to heat, so that it can be degraded to acetamide and alkyl chloride (Equation III). It reacts with alcohol in two secondary reactions to dialkyl ether, acetamide and hydrogen chloride (Equation IV), and also to dialkyl ether, acetic acid alkyl ester and ammonium chloride (Equation V). The formation of alkyl chloride is also possible through a nucleophilic substitution reaction between the alcohol and the hydrochloric acid (Equation VI).

In order to obtain a high orthoester yield, it is indispensable to suppress these secondary reactions.

In the literature citation given above, it is proposed on page 300 that the preparation of the heat-sensitive imidoester hydrochloride in accordance with Equation I be performed at very low temperatures, namely at 0° to −30° C. Ether is recommended as the organic solvent. The imidoester hydrochloride precipitated after the reaction mixture has been let stand for 48 hours is removed by suction filtering and washed with ether chilled to −40° C., and digested repeatedly with chilled ether (−40° C.) until free of acid, and then dried.

For the alcoholysis of the imidoester hydrochloride in accordance with Equation II, the procedure according to page 302 of the above-cited literature is to heat at ebullition (46° C.) for 6 hours a mixture of 0.2 mole of imidoester hydrochloride with 3 moles of alcohol (7.5 times the stoichiometrically required amount of alcohol) with the addition of ether (volumetric ratio of alcohol to ether 1:1). The reaction mixture is then cooled to 0° C. and filtered.

These procedures are not satisfactory as regards the volume-time yield. The yields are about 64 to 74%, with respect to the acetonitrile, and the reaction time—merely for the preparation of the imidoester hydrochloride—amounts to forty-eight hours.

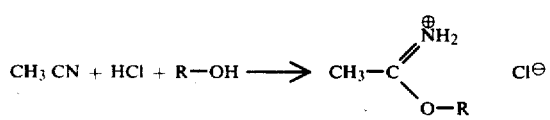

It is furthermore disadvantage that the described methods are not suitable for the preparation of orthoacetic acid alkyl esters on a commercial scale, since they are very complex and expensive. Furthermore, working with such easily combustible substances as ether requires a considerable investment in apparatus for safety reasons.

It is an object of this invention, therefore, to provide a commercially feasible process wherein orthoacetic acid alkyl esters can be prepared in yields above 74 percent employing a substantially shorter reaction time. It is an object of this invention, therefore, to provide a process for the preparation of orthoacetic acid alkyl esters from acetonitrile, hydrogen chloride and an alkanol wherein the desired orthoacetic acid alkyl ester is recovered in a high volume-time yield. It is a further object of this invention to provide a process which does not require the use of ether or other dangerous solvents and which does not require extensive working-up techniques.

SUMMARY OF THE INVENTION

In accordance with this invention there is provided such a process whereby orthoacetic acid alkyl esters are provided in a simplified and safe method in a high volume-time yield such that the same can be operated on a commercial basis. In accordance with this invention there is provided an improvement in a process for preparing an orthoacetic acid alkyl ester of the formula

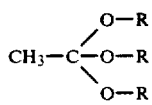

wherein R is a saturated, branched or unbranched, alkyl moiety of 1 to 8 carbon atoms by:

(a) contacting acetonitrile with anhydrous alkanol having 1 to 8 carbon atoms and dry hydrogen chloride in the presence of an organic solvent to prepare the corresponding imidoester hydrochloride;

(b) thereafter contacting said imidoester hydrochloride in the acid-free state with an alkanol having 1 to 8 carbon atoms; and (c) removing by-product ammonium chloride from the resultant reaction mixture and distilling the reaction mixture to recover orthoacetic acid alkyl ester, the improvement according to the invention residing in:

(d) employing as the organic solvent an inert solvent having a dielectric constant measured at 25° C. of 2.6 or less; and (e) contacting said imidoester hydrochloride in step (b) with an alkali metal or alkaline earth metal alcoholate before contacting the same with said alkanol.

The inert organic solvents are generally used in a weight ratio of the solvent to acetonitrile on the order of 1:1 to 5:1. Preferably, those solvents having the above-stated dielectric constants are used whose boiling points are above the working temperatures used in the practice of the method. Suitable solvents are, for example, o-, m-, or p-xylene, toluene, carbon tetrachloride, cyclohexane, n-hexane, isooctane, decaline and petroleum ether, individually or in mixtures.

The involvement of the organic solvent used in accordance with the invention in the reaction of acetonitrile with alkanols and hydrogen chloride (Equation I) makes it possible to operate at higher temperatures. Surprisingly, not only are the yields not reduced, but they are even increased if the maximum working temperatures permissible for the imidoester hydrochloride being prepared in each case are not exceeded.

In general, the temperatures in the first reaction step are from below zero to 35° C., preferably 25 to 30° C., especially in the preparation of orthoacetic acid methyl and ethyl esters. Exceeding the upper limit leads to an undesirable spontaneous crystallization of the imidoester hydrochloride, among other things.

It is desirable, in the reaction of Equation I, to operate with an excess of hydrogen chloride of about 10 mole-% with respect to acetonitrile. Too much of an excess reduces the orthoester yield, even though the excess hydrogen chloride is neutralized before beginning the alcoholysis. Optimum yields are achieved at hydrogen chloride excesses of about up to 5 mole% HCl (with respect to acetonitrile).

It has furthermore been found that the formation of acetamide in the alcoholysis of the imidoalkyl ester hydrochloride (Equation II) can be minimized if the alcoholysis is performed at temperatures below 40° C. and in the presence of the solvents or solvent mixtures used in accordance with the invention, having dielectric constants of 2.6 or less (25° C.). In general, temperatures from 30° to under 40° C., preferably of 35° C., are used, especially in the preparation of the $C_1$ and $C_2$ esters, e.g., alkyl esters.

It has also been found that the formation of acetamide and especially the formation of acetic ester also takes place beginning at 100° C. due to the action of $NH_4Cl$ on orthoacetates. If orthoacetate is heated to 100° C. in xylene in the presence of $NH_4Cl$, acetic acid alkyl ester and acetamide are formed at the expense of the orthoester. Similar conditions are encountered in the distillative working up of the reaction solution. The $NH_4Cl$ is separated prior to the distillation, by centrifugation or filtration for example, but the filtrate still contains about 1 wt-% of dissolved $NH_4Cl$, which under conditions of distillation increases the acetamide and acetic acid alkylester content. This effect is forestalled by the complete removal of the $NH_4Cl$, which is accomplished by salting out or, better, by the addition of excess alcoholate (with respect to the $NH_4Cl$ moiety) before the distillation. In a preferred embodiment of the method of the invention, therefore, provision is made for the addition of an alkali alcoholate and/or alkaline earth alcoholate prior to the distillation and after the separation of the ammonium chloride precipitated in the alcoholysis.

The alcoholate used for the deacidification of the reaction mixture prior to alcoholysis is added in such an amount that the solution is neutral to slightly basic (against methyl red).

Preferred are alkali and/or alkaline earth alcoholates which are easily soluble in the reaction solution involved. Sodium alcoholates are preferred.

The alcoholates are derived from saturated, branched or unbranched monoalkanols of one to eight carbon atoms.

The alcoholates to be added before the alcoholysis are derived from the same alcohols which are used in the first reaction step (reaction to the imidoester hydrochloride). Preferably the alcoholates to be added to the solution prior to distillation correspond to the same alcohols which have been used for the reaction and/or the alcoholysis, although fundamentally the use of other alcoholates is not to be excluded.

The alcoholate to be added prior to the distillation is generally used in a molar ratio of alcoholate to disolved ammonium chloride of one or more. Excess amounts are preferred, especially an excess of 5 to 10 mol percent.

Preferably, the same alkanols are used for the reaction of Equation I and the alcoholysis of Equation II.

The alkanol reaction component is used for the imidoalkyl ester hydrochloride formation preferably in a stoichiometric excess of up to 10 mol percent, preferably 5 mol percent, and the hydrogen chloride reaction component for the formation of imidoalkyl ester hydrochloride is used preferably in a stoichiometric excess of up to 5 mol percent.

In the alcoholysis of the imidoalkyl ester hydrochloride to the orthoacetic ester, the alkanol can be used in a stoichiometric ratio, preferably in the amount of up to one-and-one-half times the stoichiometrically necessary amount. Especially, one-and-one-quarter times the amount is used.

It is desirable to introduce the hydrogen chloride into a cooled solution of acetonitrile, alkanol and inert organic solvents, and the temperature is not to exceed approximately 10° C., preferably about 5° C., in order to prevent a premature formation of imidoester hydrochloride.

Generally speaking, step (a) (after having introduced all HCl) is performed for a period of time of between 5 and 20 hours, preferably between 9 and 13 hours. Similarly, step (b) is performed generally between 2 and 8 hours, preferably between 4 and 5 hours.

After completion of the introduction of the hydrogen chloride, the reaction temperature is raised to the optimum working temperature, e.g., 30° C., whereupon the formation of the hydrochloride begins. When the hydrochloride formation has been completed (e.g., after 10 to 15 hours of stirring the mixture), the mixture is neutralized against methyl red with the corresponding alcoholate. Then the appropriate alkanol is added for the alcoholysis of the imidoalkyl ester hydrochloride, and the mixture is stirred for 4 to 6 hours, for example, at, for example, 35° C. The $NH_4Cl$ that forms is separated, preferably removed by centrifugation, the residual $NH_4Cl$ content in the solution is determined by titration with $AgNO_3$, and the necessary amount of alcoholate, preferably an excess, is added, and fractional distillation is performed preferably after filtration.

In the reaction of Equation I and in the alcoholysis of Equation II, the reaction mixtures are best kept in constant movement, for example by means of a stirring apparatus, or by recirculation using a recirculating pump, for example.

Reaction steps 1 and 2 are performed at normal pressure. The distillative separation of the orthoacetic acid alkyl esters from the solutions can be performed at normal pressure, but it can also be performed at reduced pressure, down to, say, 10 Torr.

The organic solvent remaining in the distillation residue, xylene, for example, should be freed of acetamide, which is the principal impurity in it, by azeotropic distillation, for example, before it is reused.

The two-step reaction and the further processing of the reaction solution is best performed with the exclusion of moisture. Also, the components used should be as free of water as possible.

The yields obtained by the method of the invention are generally greater than 80 percent with respect to the acetonitrile charged. The volume-time yields are also substantially better than in the methods known hitherto. Another important advantage of the method of the invention is that the reaction and the alcoholysis can be performed straight through, i.e., without interruption of the process. For example, the isolation of the imidoester hydrochloride and the washing of it until it is free of acid is not necessary.

It is furthermore advantageous that the safe handling of the reaction solutions places no special requirements on the apparatus. In general, one operates at temperatures below the boiling point of the reaction solutions. Any solvent vapors that develop can be condensed, for example, in a refrigeration trap. If desired, however, the reaction can take place at the ebullition temperature, in which case reflux condensers are used.

Orthoacetic acid alkyl esters are valuable intermediates for organic syntheses, especially for the production of pharmaceuticals and insecticides.

In order to more fully illustrate the nature of the invention and the manner of practicing the same, the following examples are presented.

EXAMPLES

EXAMPLE 1

A solution of 845 g (20.61 moles) of acetonitrile and 692 g (21.63 moles) of methanol in 1500 g of o-xylene is chilled to $-10°$ C. and then, over a period of 100 minutes, 789 g (21.62 moles) of anhydrous hydrogen chloride is introduced directly into the solution, with stirring, the temperature rising to $+10°$ C. After the hydrogen chloride introduction is completed, the reaction solution is heated to 30° C.; after about 3 hours the imidomethyl ester hydrochloride crystallizes out; then stirring is continued for 8 hours at 30° C. Then 1530 g (47.8 moles) of methanol is added for the methanolysis, and the excess HCl is neutralized against methyl red with 130 g of a 30 wt.-% methanolic solution of $NaOCH_3$. After the neutralization, the temperature is raised to 35° C. and stirring is continued for another four hours. Then the mixture is cooled down to 10° C. and the $NH_4Cl$ is removed by centrifugation. The solid substance is washed with o-xylene and the residual content of dissolved $NH_4Cl$ (0.2298 mole) in the combined filtrate is determined by titration with $AgNO_3$, and then $NaOCH_3$ is added in an excess (43 g of a 30% solution of $NaOCH_3$ in methanol). From the filtrate thus treated, fractionation through a packed column yielded 2134 grams Trimethylorthoacetate (17.79 moles = 86.3% yield with respect to the $CH_3CN$ put in, 90% yield with respect to reacted $CH_3CN$), boiling point 108°–109° C.

The o-xylene remaining in the distillation residue contains acetamide as the main impurity, which is removed by azeotropic distillation. The o-xylene thus purified can be reused.

EXAMPLE 2

A mixture of 410 g (10.0 moles) of acetonitrile, 336 g (10.5 moles) of methanol and 1000 g of isooctane is refrigerated down to $-10°$ C. and over a period of 90 minutes 383 g (10.5 moles) of anhydrous hydrogen chloride is introduced directly into the solution, with stirring, so that the temperature increases to $+5°$ C.

When the hydrogen chloride introduction is completed the mixture is heated to 30° C. After about 2 hours the imidomethyl ester hydrochloride crystallizes out, and then stirring is continued for another 10 hours at 30° C. Then 800 g (25 moles) of methanol is added for the purpose of methanolysis, and the excess HCl is neutralized against methyl red with 66 g of a 30% solution of NaOCH₃ in methanol. After the neutralization, the temperature is raised to 35° C. and stirring is continued for five more hours. Then the mixture is chilled to 0° C. and the NH₄Cl is centrifuged out. The solid is washed with isooctane, and the residual content of dissolved NH₄Cl (0.075 mole) in the combined filtrate is determined by titration with AgNO₃, and then NaOCH₃ is added in an excess with respect to the dissolved NH₄Cl (14 g of a 30% solution of NaOCH₃ in methanol).

The filtrate thus treated is subjected to a fractional distillation. First the low-boiling components and isooctane pass over, and then the trimethyl orthoacetate is removed through the top of the column. The remaining crystalline residue, which consists mostly of acetamide, is washed once again with isooctane to remove orthoester residues which are combined with a subsequent batch for working up.

Yield of orthoacetic acid methyl ester: 1028 g (8.57 moles) = 85.7% with respect to the acetonitrile put in, 89.5% with respect to reacted acetonitrile.

EXAMPLE 3

410 g (10 moles) of acetonitrile and 483 g (10.5 moles) of ethanol are dissolved in 900 g of decaline and the mixture is cooled to −10° C. With stirring, 383 g (10.5 moles) of anhydrous hydrogen chloride is introduced directly into the solution. The HCl introduction period amounts to 80 minutes, the temperature increasing, despite continued refrigeration, to +7° C. After completion of the HCl introduction, the temperature is raised to 30° C.; after 2.5 hours the imidoethyl ester hydrochloride crystallizes out; then stirring is continued at 30° C. for another 11 hours. 1150 grams of ethanol (25 moles) is then added to the solution and it is neutralized against methyl red with 115 g of a 20% solution of sodium ethylate in ethanol. After the neutralization, the temperature is raised to 35° C. and the mixture is stirred for 5 hours. After it has been chilled to 10° C., the ammonium chloride is centrifuged out and washed with decaline. The combined filtrates are treated, after chloride determination (titration with AgNO₃), with an appropriate excess of sodium ethanolate (35 g of 20% solution of sodium ethanolate in ethanol). The filtrate thus treated is distilled in vacuo in a packed column. 1414 g of triethyl orthoacetate (B.P. 66°-68° C. at 41 Torr) is obtained (8.73 moles = 87.3% with respect to acetonitrile input and 91.2% with respect to reacted acetonitrile). After the acetamide has been filtered out of the sump phase, the decaline thus purified can be reused.

What is claimed is:

1. A process for preparing an orthoacetic acid alkyl ester of the formula

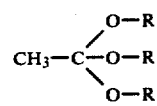

wherein R is a saturated, branched or unbranched, alkyl moiety of 1 to 8 carbon atoms which comprises:
   (a) contacting acetonitrile with an anhydrous alkanol having 1 to 8 carbon atoms and dry hydrogen chloride in the presence of an inert organic solvent having a dielectric constant measured at 25° C. of 2.6 or less at a temperature of up to 35° C. to prepare the corresponding imidoester hydrochloride;
   (b) thereafter, without isolating said imidoester hydrochloride, contacting the reaction mixture of step (a) with an alkanol having 1 to 8 carbon atoms and deacidifying the reaction mixture before raising to 30° C. to less than 40° C. with an alkali metal or alkaline earth metal alcoholate in an amount sufficient to adjust the alkalinity of the reaction mixture so that it is neutral or slightly basic against methyl red, said alcoholate being an alcoholate of the same alcohol employed in step (a);
   (c) raising the mixture to a temperature of 30° C. to less than 40° C.; and
   (d) removing by-product ammonium chloride from the resultant reaction mixture and distilling the reaction mixture to recover orthoacetic acid alkyl ester.

2. A process according to claim 1 where following the contacting of said imidoester hydrochloride with said alcohol and removal of ammonium chloride in step (d) but prior to the distillation of step (d) there is added to the reaction product of step (b) additional alkali metal or alkaline earth metal alcoholate.

3. A process according to claim 2 where the alcoholate added prior to said distillation and after ammonium chloride removal is used in an alcoholate to dissolved ammonium chloride molar ratio equal to or greater than one.

4. A process according to claim 1 wherein said alcoholate is a sodium alcoholate.

5. A process according to claim 1 wherein step (a) is performed at a temperature of 25° to 30° C.

6. A process according to claim 5 wherein step (b) is performed at a temperature of 35° C.

7. A process according to claim 1 wherein the weight ratio of said organic solvent to acetonitrile is 1–5:1.

8. A process according to claim 7 wherein said solvent is selected from the group consisting of o-, m-, p-xylene, toluene, carbon tetrachloride, cyclohexane, n-hexane, isooctane, decaline, and petroleum ether, individually or in mixtures.

* * * * *